United States Patent [19]

Würzburg et al.

[11] 4,237,044
[45] Dec. 2, 1980

[54] ANTIBODIES AGAINST CREATINEKINASE-M8 AND PROCESS FOR THE PRODUCTION THEREOF

[75] Inventors: Uwe Würzburg; Norbert Hennrich; Hans-Dieter Orth; Hermann Lang, all of Darmstadt, Fed. Rep. of Germany

[73] Assignee: Merck Patent Gesellschaft mit beschränkter Haftung, Darmstadt, Fed. Rep. of Germany

[21] Appl. No.: 37,191

[22] Filed: May 8, 1979

Related U.S. Application Data

[63] Continuation of Ser. No. 737,264, Nov. 1, 1976, abandoned.

[30] Foreign Application Priority Data

Nov. 3, 1975 [DE] Fed. Rep. of Germany ....... 2548962

[51] Int. Cl.$^3$ ..................... A61K 39/395; C07G 7/00; G01N 33/68
[52] U.S. Cl. .............................. 260/112 B; 23/230 B; 260/112 R; 424/8; 424/12; 424/85
[58] Field of Search ....................... 424/8, 12, 85, 177; 260/112 R, 112 B; 23/230 B; 435/7

[56] References Cited

U.S. PATENT DOCUMENTS

| | | | |
|---|---|---|---|
| 3,932,221 | 1/1976 | Pfleiderer | 424/2 X |
| 4,012,285 | 3/1977 | Pfleiderer | 424/2 X |
| 4,067,775 | 1/1978 | Wurzburg | 424/12 X |

OTHER PUBLICATIONS

Mercer, Clin Chem vol. 20, No. 1, 1974 pp. 36–40.
Pfleiderer, Clin Chem Acta, vol. 58 No. 3, 1975 pp. 223–232.
Henry, Clin Chem, vol. 21, No. 7, 1975 pp. 844–848.
Roy, Biochem J vol. 143, 1974 pp. 171–179.
Eppenberger, J. Biol. Chem., vol. 242, 1967 pp. 204–209
Armstrong, Diss. Ab, vol. 36, No. 10 (B) p. 4987–B.
Williams, Methods in Immunol. & Immunochem. Acd Press, NY vol. I, 1967 pp. 205–221, 237–244.
Dawson, J of Biol. Chem. vol. 242, 1967 pp. 210–217.
Wurzburg, J Clin. Chem. Clin. Biochem; vol. 15, 1977 pp. 131–137.

Primary Examiner—Anna P. Fagelson
Attorney, Agent, or Firm—Millen & White

[57] ABSTRACT

Antibodies against the M subunit of CK isoenzymes having a molecular weight between about 130,000 and 210,000, and inhibiting the enzymatic activity of the M subunit, optionally also in the presence of CK substrates, without inactivating the enzymatic activity of the B subunit of any CK-MB which may be present, are described. A process for the production of these antibodies comprises inoculating animals with activated CK-MM and recovering the antibodies in a conventional manner.

18 Claims, No Drawings

ANTIBODIES AGAINST CREATINEKINASE-MB AND PROCESS FOR THE PRODUCTION THEREOF

This is a continuation, or application Ser. No. 737,264 filed Nov. 1, 1976, now abandoned.

REFERENCE TO RELATED APPLICATION

U.S. application Ser. No. 737,587, filed concurrently with the parent of the present application, and now U.S. Pat. No. 4,067,775, issued Jan. 10, 1978, is addressed, inter alia, to uses of the antibodies of this invention.

BACKGROUND OF THE INVENTION

This invention relates to antibodies specific for cretinekinase-MB antibodies and a process for the production thereof.

The determination of the activity of creatinekinase (ATP: creatine-phosphotransferase, E.C. 2.7.3.2; abbreviation: CK) in serum is considered the most sensitive laboratory method for diagnosing diseases of skeletal muscles and the myocardium, especially in the case of myocardial infarction. However, differentiation between trauma of skeletal muscles and the myocardium is difficult, especially in making a differential diagnosis of myocardial infarction. Reliable differentiation is impossible by a determination of the total CK activity. Therefore, attempts have been made to increase the reliability of the evidence provided by measurement of CK activity in differential diagnosis by measuring the activity of other enzymes in the serum and correlating the resulting measurements with each other, for example, by forming the quotient CK/glutamic oxalacetic transaminase. However, quotients of this type cannot be used to differentiate between cardiac infarction and pulmonary infarction or between cardiac infarction and secondary shock resulting from other causes.

CK occurs in the body in the form of three isoenzymes, namely CK-MM, for example, in muscles; CK-BB, for example, in the brain; and as a hybrid CK-MB, consisting of an M and a B subunit, for example, in the myocardium. The CK activity occurring in the blood serum is normally due to the CK-MM isoenzyme, because CK-BB does not pass through the fluid/blood barrier and CK-MB is restricted to certain organs, for example, the myocardium. However, in case of damage to the myocardium as in the case of cardiac infarction, CK-MB is released into the blood serum and can be detected therein.

Quantitative determination of this isoenzyme along with CK-MM in the serum is considered the most sensitive laboratory method and is of the greatest value in differential diagnosis of cardiac infarction. Although a few other organs, in addition to the myocardium, contain CK-MB, e.g., the pancreas, the diaphragm, the aorta, the lungs, and the uterus, the activity of these organs is less by a factor of 100 than in the myocardium, so that any CK-MB activity liberated from the aforementioned organs is below the limits of detection.

Heretofore, activity determinations of CK-MB were based primarily on electrophoretic and chromatrographic methods, or on immunological determinations with antibodies to cause precipitation. All of these methods had the feature in common that they were unsuitable for a rapid diagnostic determination of CK-MB activity.

This invention is based on the development of antibodies, with which it is possible to conduct a quantitative determination of CK-MB activity, especially a rapid determination of activity of this isoenzyme in body fluids.

This problem is solved, in accordance with the invention, by the production of heretofore unknown highly specific antibodies against the subunit M of CK-MM and CK-MB.

SUMMARY OF THE INVENTION

In a compositional aspect, this invention relates to antibodies completely able to inhibit the enzymatic activity of the M subunit of creatinekinases MM and MB without inactivating the enzymatic activity of the B subunit of any creatinekinase-MB in the sample, wherein complete inhibition of said M subunit leaves less than 5 U./l. of said enzymatic activity intact and non-inhibition of said enzymatic activity of said B subunit is less than 10 U./l., wherein said anitbodies are substantially free of CK-BB isoenzyme activity and have a molecular weight of 130,000–210,000 and a sedimentation constant between 6 S and 8 S.

In a process aspect this invention relates to a method of producing the antibodies which comprises the steps of activating a CK-MM antigen by an activator for —SH groups such as N-acetylcysteine, mercaptoethanol, dithioerythritol, glutathione, cysteine, dithiothreitol, S-(2-aminoethyl)-isothiouronium bromide hydrobromide or thioglycolic acid or a divalent metal ion activator selected from magnesium, manganese, calcium or cobalt, or a mixture of activators; inoculating an animal with the thus-activated CK-MM antigen; withdrawing blood from the aminal; and isolating said antibodies from the withdrawn blood.

In a method of use aspect, this invention relates to the improvement of using the foregoing antibodies in a method for determining the activity of creatinekinase-MB in addition to creatinekinase-MM in a biological sample.

DETAILED DESCRIPTION

The antibodies of this invention are obtained from animals inoculated with CK-MM antigens. Human CK-MM is most preferably used as the antigen. CK-MM from animals can also be used, if the antisera prepared therewith are able to inhibit completely the enzymatic activity of the M subunit in human CK-MM and CK-MB, optionally in the presence of CK substrates, without inactivating the enzymatic activity of the B subunit of any CK-MB present therein. Animal donors of CK-MM antigens include, for example, all the various species of monkeys, preferably Rhesus monkeys and chimpanzees; domestic animals, such as pigs, horses, cattle, rabbits, or guinea pigs; and other animals, e.g., rats or mice; and birds, such as geese, ducks, or chickens. Monkeys, pigs or cattle are preferred.

The CK-MM antigen used to produce the antibodies must be free of CK-MB and CK-BB activities. A sensitive criterion of this purity requirement is immunological analysis as carried out by diffusion or electrophoresis techniques. In addition, for example, analytical disc electrophoresis and polyacrylamidegel electrofocusing are useful. Determination of the purity with respect to CK-MB and CK-BB takes precedence over absolute purity with respect to other proteins detectable, for example, by two last-mentioned methods. The microheterogeneity of CK isoenzyme types, which is manifested, for example, in minor differences in the amino acid composition of the individual CK subunits, is as a rule of no importance as a purity criterion.

The CK-MM antigen used is freed from CK-MB and CK-BB, if necessary, according to a method described by Donald W. Mercer in Clin. Chem., 20: 36–40 (1974).

To obtain the antibodies, animals are employed which, after inoculation with activated CK-MM, form antibodies capable of entirely inhibiting the enzymatic activity of the M subunit in the creatinekinases MM and MB without inactivating the enzymatic activity of the B subunit in any CK-MB present therein. Goats are preferred for this purpose. However, other animals suitable as antibody donors, include, for example, other vertebrates, e.g., species of monkeys; horses; cattle and bovine animals, sheep; dogs; pigs; rabbits; birds such as chickens, turkeys, geese, and ducks; and rats, mice and guinea pigs. Goats are used especially for the induction of antibodies which are able to exert complete inhibition of the M subunit in CK-MM and CK-MB, even in the presence of CK substrates.

The inoculation of the animals takes place according to otherwise conventional methods; except that, according to the invention, the immunization is conducted with activated human or animal CK-MM. Activation of the CK-MM utilized herein can be effected by known reagents which stabilize and activate SH-groups and/or by divalent metal ions, preferably by a combination of the aforementioned reagents and of the metal ions. Preferred reagents which stabilize and activate SH-groups are, for example, N-acetylcysteine, mercaptoethanol and dithioerythritol, as well as glutathione, cysteine, dithiothreitol, S-(2-aminoethyl)-isothiouronium bromide hydrobromide (AET) and/or thioglycolic acid. The divalent metal ions originate from corresponding water-soluble salts, for example, chlorides or acetates, preferably of magnesium, or of manganese, calcium and/or cobalt. Activation of this type is known basically in other fields and are familiar to those skilled in the art. A preferred combination of activators is magnesium ions and one of N-acetyl-cysteine, mercaptoethanol or diethioerythritol.

It is possible to activate the antigen by treating CK-MM with activating reagents which stabilize and activate SH-groups and/or with divalent metal ions. Conventional dialysis methods are preferably utilized. It is thus possible, for example, to dialyze the antigens employed against a buffered solution containing the activating substances during a period of 1–200 hours, preferably during about 12 hours, at temperatures of between 1° and 30° C., preferably at about 4° C. Suitably, the dialysis solution is based on physiological sodium chloride solution. In principle, any buffer suitable for setting a pH of 6.5–7.5, preferably 6.8–7.0, can be used. In addition to sodium phosphate buffers, triethanolamine (TRAM), tris(hydroxyethyl)-amine (TRIS), and imidazole buffer pH 6.8, can be used. The solution containing the antigen is to contain about 10–500 millimoles of the compound which stabilizes and activates SH-groups and/or about 50–500 millimoles of the divalent metal ions per milligram of CK-MM.

The subsequent immunization and the isolation procedure to obtain the antisera or antibodies takes place conventionally. The processing and storage of the antisera or antibodies is carried out by methods known in immunology.

Antibodies of the invention are preferably to be assigned to the category of IgG immunoglobulin (bivalent antibodies). Their molecular weight ranges between about 130,000 and 210,000, preferably being about 160,000–180,000, as determined by conventional methods; their approximate sedimentation constant is between 6 S and 8 S, preferably about 7 S, as determined by analytical ultracentrifugation; their carbohydrate content is about 3% of their total weight, determined by the methods described in "Handbook of Experimental Immunology" ed. by D. M. Weir, 2nd edition 1973, pages 10.45–10.58, Blackwell Scientific Publications.

The antibodies of the invention are able to completely inhibit the enzyme activity of the M subunit of creatinekinase. In this context, "complete inhibition" means an inhibition with which, on the average, at most 5 U./l., preferably less than 3 U./l., of the enzyme activity of the M subunit in CK-MM and CK-MB remains intact in a sample.

The antibodies thus-produced do not affect the enzymatic activity of the B subunit in CK-MB. This means that at most 10 U./l., preferably less than 5 U./l. of the enzyme activity of the B subunit in CK-MB are inhibited in a sample.

The invention also relates to the use of these antibodies for determining the activity of CK-MB beside CM-MM, especially in a differential-diagnostic laboratory test for the detection of cardiac infarction.

Such a test can be conducted by incubating a sample of a body fluid, optionally in the presence of CK substrates, with the antibodies of this invention and determining by photometry the activity of the CK subunit B in a conventional manner.

In this connection, body fluid means primarily human serum, but also furthermore whole blood, plasma, urine, sputum, and perspiration. CK-BB interferes with the testing method conducted with the antibodies of this invention; therefore, this isoenzyme must be absent from the body fluids being analyzed.

In a preferred embodiment of the process conducted with the antibodies of this invention, the sample of body fluid to be analyzed and the antibodies are incubated in the presence of CK substrates and the antibodies furthermore are able to exert their inhibitory effect with respect to the enzymatic activity of the M subunit in CK-MM and CK-MB even in the presence of CK substrates without influencing the enzymatic activity of the B subunit of any CK-MB present. This property is present in addition to the above-characterized properties, for example, in antibodies obtained from goats by immunization with fully activated CK-MM. This property is not absolutely essential in carrying out the process in the normal manner, by first incubating with antibodies and then adding CK substrates and conducting a photometric measurement.

CK substrates which can be employed are customary substrates and/or effectors, particularly creatine, creatine phosphate, adenosine diphosphate, adenosine triphosphate, and magnesium ions.

Determination of the activity or residual activity of CK and the isoenzymes thereof can be conducted by any processes which are rapid and precise. Suitable are, for example, conventional methods of measuring CK activity after the addition of CK substrates by photometric analysis following auxiliary reactions. For this purpose, colorimetric methods can be employed, as described, for example, in "Methoden der Enzymatischen Analyse", Methods of Enzymatic Analysis, edited by H. U. Bergmeyer, 3rd edition (1974), 1: 145 et seq. However, kinetic methods are preferred wherein the anzyme activity is determined by measurement in UV at, for instance, 334, 340, or 366 nm. In particular, a standard method is utilized, for example, accordingly to which CK is determined with the use of creatine phosphate and adenosine diphosphate, "Z. Klin. Chem. Klin. Biochem." Periodical for Clinical Chemistry and Clinical Biochemistry, 8: 658 et seq. (1970) and 10: 182 (1972). Test kits to determine the CK activity by this method are available commercially.

In accordance with another known method of analysis, CK can also be determined by fluorometry. Creatine can be liberated from creatine phosphate by means of CK, and this creatine can be measured fluorometrically in accordance with the method developed by R. B. Conn, Clin. Chem., 6: 537 et seq. (1960), by reaction with nihydrin in a strongly alkaline solution, See, Sax et al., Clin. Chem., 11: 951 et seq. (1965).

A typical possibility of utilizing the antibodies of this invention will be described hereinbelow:

A quantity of CK-MM antibodies is combined with the sample of body fluid to be analyzed, preferably a specimen of human serum, which is sufficient to inhibit completely up to 2500 U./l. of the M subunit in CK-MM and CK-MB, preferably about 1000 U./l. The mixing and incubation is carried out during a period of about 1–30 minutes, preferably about 5 minutes, at temperatures of between $+10°$ and $+40°$ C., preferably approximately at room temperature, specifically at 25° or 30° C. Thereafter, the residual enzyme activity of the reaction mixture is determined by a known procedure, preferably by the UV method described above.

This process can be modified by incubating the sample of body fluid to be analyzed together with the antibodies and the CK substrates in the presence of a buffer and the compounds required for the detection reaction, without preliminary incubation of the sample with the antibodies. A prerequisite for this procedure is that the antibodies of the invention have an additional property: they must completely inhibit the enzymatic activity of the M subunit of CK-MM and -MB even in the presence of CK substrates, as displayed, for example, by the antibodies obtained according to the process of this invention from goats. They make it possible to conduct the determination of the CK-MB activity in a simple and rapid fashion.

It is possible, for example, to dissolve the antibodies, previously lyophilized with the known coenzyme-enzyme substrate mixture utilized for the analytical reaction, for example, a mixture containing as the coenzymes adenosine diphosphate and nicotinamide adenine dinucleotide phosphate; as enzymes hexokinase and glucose-6-phosphate dehydrogenase; and as substrates creatine phosphate and glucose, in a specific amount of a buffer solution; then to add the body fluid to be analyzed, e.g., serum; and to conduct the activity determination of the B proportion of CK-MB. In a modification of this method, the antibodies can also be incorporated into the lyophilized product with a mixture consisting merely of coenzymes and enzymes. Then the substrates of the buffer solution are added thereto.

According to another modification, the antibodies of this invention can be utilized in a single batch for simultaneous determination of the total CK activity and of the CK-MB activity. The procedure can be such, for example, that first the total CK activity of the sample is determined according to a conventional photometric procedure; thereafter, a lyophilized product, dissolved in water, is added to the same batch, this lyophilized product consisting of the antibodies of this invention. The incubation is then carried out for about 1–10 minutes, preferably 5 minutes, and the residual activity of the sample is determined by photometry. The antibodies against CK-MM used for this purpose are to have the property of completely inhibiting the enzyme activity of the M subunit of CK-MM and -MB even in the presence of CK substrates.

The antibody capacity of the antisera, in this embodiment, can be adjusted so that a complete inhibition of the M subunit in CK-MM and -MB is effected, up to 2500 U./l., preferably about 1000 U./l.

The CK-MB determination method made possible by the antibodies of the invention has considerable advantages over the prior art. Among these advantages are the high precision of the results and the rapidity, as well as the simplicity of the process.

The precision in the analysis is due to the fact that the antibodies of the invention respond specifically to the M subunit of CK-MM and CK-MB, thus making is possible to determine the CK-MB activity in body fluids, such as human serum, directly.

Reference is made to the copending U.S. application of U. Wuerzburg, et al., Ser. No. 737,587, now U.S. Pat. No. 4,067,775, issued Jan. 10, 1978, filed on even date herewith, describing the preparation of anti-CK-MM, whose disclosure is incorporated by reference, and to the corresponding German Patent Application P No. 25 48 963, filed Nov. 3, 1975.

In a most preferred embodiment, the antibodies of this invention are substantially free of CK-BB isoenzyme activity and have a molecular weight of 160,000–180,000; and are able to effect complete inhibition of said enzymatic activity of said M subunit in CK-MM and CK-MB without inhibiting said enzymatic activity of said B subunit, even in the presence of a CK substrate; complete inhibition of the enzyme activity of said M subunit of creatinekinease leaves less than 3 U./l. of said enzymatic activity intact and non-inhibition of said enzymatic activity of said B subunit is less than 5 U./l.

In a most preferred aspect, the method of this invention is that wherein the CK-MM antigen is from skeletal muscle of humans, monkeys, pigs or cattle and is activated by dialysis against the activator in the presence of a dialysis buffer for 1–200 hours at 1–30° C.; said inoculated animal is a goat; 10–500 mM of activator is used per mg. of creatinekinase-MM being activated; and the activator is magnesium ions and N-acetylcysteine, mercaptoethanol or dithioerythritol.

In contract thereto, in the immunological methods for the determination of isoenzymes disclosed in German Patent Applications P, No. 21 28 670 and P No. 22 58 822, at least two different test batches must be prepared for analysis, namely the determination of the total CK activity and the determination of the residual CK activity after precipitation. Thus, the CK-MB activity can only be determined by a differential measurement. According to the rules of the theory of errors, the result is according burdened by the unreliability of both measurements. In contrast thereto, the method conducted with the antibodies of this invention makes it possible to avoid additive errors.

Another disadvantage of the precipitation method is that the immune precipitation, as a secondary reaction, takes a relatively large amount of time, about 60 minutes up to several hours, so that the process is unsuitable as a rapid test.

In Clin. Chem. Acta, 58: 223-232 (1975), inhibiting antibodies against CK isoenzymes have already been described. These antibodies effect, in addition to a 100% inhibition of CK-MM, simultaneously an 80% inhibition of CK-MB. Therefore, above and beyond an inhibition of the M subunit of CK-MB, an essential proportion of the B subunit is likewise inhibited by the antibodies employed. The activities of the M and B subunits in CK-MB are, as related to the total activity of this isoenzyme, respectively about 50: 100. Even if the residual activity of about 20% found with these antibodies were reproducible, the thus-obtained values still would be too low for a precise measurement of CK-MB as to be reliably detectable, since the total CK activity in the serum per se is already low. The inhibiting antibodies described in this literature reference correspondingly have not been utilized, for a determination of the CK isoenzymes according to the inhibition principle. In contrast thereto, with the use of the process conducted with the antibodies of this invention, still approximately 50% of the CK-MB activity is preserved, i.e., approximately the entire activity of the B subunit, for the measurement. This represents considerable progress.

A special advantage of the method which can be carried out with the antibodies of this invention is the fact that it can be effected with great speed. This is true, in particular, for the modification of the method according to which the inhibition of the M portion of CK-MM and CK-MB, as well as the determination of the residual activity, are conducted at the same time. According to this modification, an exact test result can be available for rendering the diagnosis within a minimum time, for example, within 5-30 minutes, preferably between 5 and 15 minutes.

A considerable advantage of the method which can be conducted with the antibodies of this invention is its simplicity. The testing method can be carried out in larger institutions or clinics, for example, with customary mechanical appliances for the determination of enzyme activities, but it can also be accomplished in smaller institutions and/or in the physician's laboratory with a photometer.

For individual analyses, test kits are suitable which contain all of the reagents necessary for conducting the CK determination method, thus, for example, a customary mixture of coenzyme, enzyme, and substrate, CK-MM antibodies according to this invention, and a buffer solution. A test kit of this or a similar type makes it possible to determine CK-MB with a minimum expenditure of time.

It is unexpected that it would be possible to produce specific antisera which, though inhibiting the enzymatic activity of the M subunit in CK-MM and -MB entirely, do not affect the enzymatic activity of the B subunit of CK-MB. The use of the antibodies of this invention having these heretofore unknown properties, however, is the prerequisite for making above-described, simple method for the determination of CK-MB feasible.

It is also surprising that the antibodies according to the invention retain their full inhibitory power even in the presence of substrates. This is not commonplace. Thus, antibodies have been described in the literature, Ann. N.Y. Acad. Sci., 103: 858-889 (1963), which no longer inactivate CK-MM to an extent of 100% in the presence of CK substrates. Antibodies having such properties would be completely useless for the modified embodiment of the analysis method which can be carried out with the antibodies of this invention, according to which the antibody inhibition and the addition of CK substrates take place simultaneously. The uninhibited proporations of the M activities would falsely increase the measured value of CK-MB; and simulate CK-MB activities which perhaps are not present at all. In this way, erroneous laboratory data would be produced.

The surprising property of the antibodies of this invention of entirely inhibiting the enzymatic activity of the M subunit of CK-MM and -MB without affecting the enzymatic activity of the B subunit of CK-MB and of simultaneously displaying their full inhibitory power with respect to the M subunit in CK-MM and CK-MB in the presence of substrates makes it possible to provide a rapidity and precision in the CK-MB activity analysis which heretofore has been unattainable by immunological methods. Thereby, a path has been opened up for a practical determination of CK-MB activity by means of an instant test.

It has become possible to differentiate the laboratory finding of an increase in the CK activity in a patient so that it is possible to determine whether a disease or trauma is present in the skeletal muscles or in the myocardium. Thereby, important additional data are obtained for the differential diagnosis of cardiac infarction, e.g., from pulmonary infarction and/or secondary shock, and other diseases and/or damage of the heart.

Moreover, due to the specific and exact determination of the CK-MB activity, data are obtained regarding the extent to which the myocardium is involved or damaged in case of other, extracardial disease processes, for example, in case of poisoning or accidents; in therapeutic interventions, e.g., during resuscitation procedures; or in case of diagnostic interventions, e.g., in case of cardiac catheterizations or coronary angiographies.

In the following examples, "M" or "mM", respectively, mean the concentrations in moles or millimoles, respectively, per liter.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

PREPARATION OF THE STARTING MATERIALS

EXAMPLE A

Preparation of CK-MM (a) 1.2 kg. of deep-frozen human skeletal muscle is thawed at room temperature and mechanically comminuted. The tissue is suspended in 2.5 l. of cold 0.05-molar TRIS/HCl buffer, pH 8.0 (tris(hydroxymethyl)aminomethane-HCl buffer) containing 0.01 M KCl, 1 mM EDTA (ethylenediaminetetraacetic acid), and 1 mM dithioerythritol, and homogenized in a mixer. The homogenized product is stirred with ice cooling for 45 minutes and then centrifuged for 60 minutes at 12,000 g.'s. The clear supernatant liquor (2:608 l.) is subjected to an ammonium sulfate fractionation at pH 8.0 within the limits of 40-75% saturation. The 0.75 s-precipitate is taken up in 0.04-molar TRIS/HCl buffer, pH 8.0, and dialyzed against the same buffer. To absorb myoglobin and acidic ballast proteins, 500 g. of moist basic ion exchange resin based on crosslinked dextran, equilibrated against the same buffer, is added thereto. After 30 minutes, the exchanger is filtered off and washed twice with, respectively, 400 ml. of 0.04-molar TRIS/HCl buffer, pH 8.0, containing 0.02 M NaCl. The filtrate and the wash water are combined and brought to 0.75 s with ammonium sulfate. The precipitate is removed by centrifuging, dissolved in 100 ml. of 0.04-molar TRIS/HCl buffer, pH 8.0, and dialyzed against the same buffer until no more ammonium sulfate can be detected. The clear dialyzed product is equilibrated with the same buffer on a column with a basic ion exchange resin based on crosslinked dextran (6×60 cm). The column is washed with starting buffer until the eluate is free of protein. Thereafter, the enzyme is eluted from the column with 0.04-molar TRIS/HCl buffer, pH 8.0, containing 0.02 M NaCl, 1 mM EDTA, and 1 mM dithioerythritol. Fractions with an enzyme content of at least 20 U./ml. are combined, saturated to 80% with ammonium sulfate, and the precipitated enzyme is removed by centrifuging. For purposes of final purification, the enzyme is once again subjected to a chromatography in the same system, but with the use of a smaller column volume. From the combined active fractions, the enzyme is precipitated with 0.8 s ammonium sulfate, dissolved as a concentrated solution in 50 ml. of 0.04-molar TRIS/HCl buffer, pH 8.0, containing 0.02 M NaCl, 1 mM EDTA, and 1 mM dithioerythritol, filtered under sterile conditions, and again brought to 0.8 s with ammonium sulfate, thus obtaining an enzyme suspension, stable at 4° C., of CK-MM with a specific activity of 26–30 U./mg., measured with creatine as the substrate at 25° C.

Volume: 86 ml.; activity: 316 U./ml.; protein: 11.8 mg./ml. Yield: about 30%, based on the organ extract.

EXAMPLE B

Analogously to Example A, CK-MM is isolated from the muscle tissue of the following animals: Rhesus monkeys, pigs, cattle.

EXAMPLE 1

CK-MM from human muscle, obtained according to Example A(a), is dialyzed against a physiological NaCl solution buffered with 0.07-molar triethanolamine, pH 7.0, containing 10 mM mercaptoethanol and 10 mM $MgCl_2$. The enzyme solution is freed of aggregates by ultracentrifuging, and the protein content is adjusted with the aforementioned dialysis buffer to 2 mg./ml. One milliliter of this solution is emulsified with 1 ml. of complete Freund's adjuvant, a water-mineral oil suspension additionally containing 2 mg. of killed M-tuberculosis bacilli. This emulsion is injected intramuscularly into a goat. After three injections of the same type at intervals of 3 weeks, and another three booster injections, respectively at an interval of 16 weeks, blood is withdrawn from the animal 21 days after the last injection. The serum, obtained according to conventional methods, is adjusted to pH 8.4 with a mixture containing 3% sheep serum albumin and 0.1% sodium azide, with the use of a 0.1-molar borate buffer, and then filtered under sterile conditions. The thus-obtained solution, containing anti-human muscle-CK-MM, is dispensed into brown glass bottles in 0.5 ml. portions and freeze-dried. The antibodies have a molecular weight of about 160,000 to 180,000.

EXAMPLE 2

CK-MM from human muscle is dialyzed against a physiological NaCl solution, pH 6.8, buffered with 0.1-molar imidazole, containing 7.5 mM N-acetylcrysteine and 25 mM magnesium acetate. Thereafter, the enzyme solution is freed of aggregates by ultracentrifuging, and the protein content is adjusted to 0.2 mg./ml. with the aforementioned dialysis buffer. One milliliter of this solution is emulsified with 1 ml. of complete Freund's adjuvant. This emulsion is injected into a ram intradermally. After 3 and 6 weeks, two intramuscular injections are administered, and three further booster injections, respectively at an interval of 14 weeks. Nineteen days after the last injection, blood is taken. The isolation process takes place as described in Example 1, thus obtaining anti-human muscle-CK-MM in a freeze-dried form. The molecular weight of the antibodies is about 160,000 to 180,000.

EXAMPLE 3

CK-MM from Rhesus monkey muscle, obtained according to Example B, is dialyzed against a physiological NaCl solution, pH 6.8, buffered with 0.15-molar imidazole, containing 25 mM dithioerythritol and 15 mM manganese chloride. After the aggregates have been removed by ultracentrifuging, the protein content is adjusted to 5 mg./ml. with the aforementioned dialysis buffer. One milliliter of this solution is emulsified with 1 ml. of complete Freund's adjuvant. The injections, blood taking, and working-up procedures take place according to Example 1, thus obtaining anti-Rhesus monkey muscle-CK-MM in a freeze-dried form. Sedimentation constant of the antibodies: about 7 S.

EXAMPLE 4

CK-MM from pig's muscle is activated analogously to Example 2, and the antigen emulsion is injected into rabbits together with complete Freund's adjuvant. After three weeks, another subcutaneous antigen injection is effected. The injection is repeated after another three weeks, and 19 days thereafter blood is withdrawn. The isolation process takes place analogously to Example 1, thus obtaining anit-pig muscle-CK-MM in a freeze-dried form. The molecular weight of the antibodies is about 160,000 to 180,000.

In a completely analogous way, anti-beef muscle-CK-MM is obtained from beef muscle, molecular weight about 160,000 to 180,000.

Application Example I

Test I for the quantitative determination of the activity of CK-MB in body fluids.

(a) Composition of the Test Kit

The test kit is sufficient for 10 activity analyses. The kit comprises 1 bottle of buffer for 10 analyses, 10 bottles of coenzyme-enzyme substrate mixture, and 1 bottle of anti-CK-MM, obtained according to Example 1.

The bottle with the coenzyme-enzyme substrate mixture contains:

| | | |
|---|---|---|
| Creatine phosphate disodium salt, hexahydrate | 27.24 | mg. |
| Glutathione, reduced | 6.4 | mg. |
| (or N-Acetylcysteine) | 3.4 | mg.) |
| Adenosine diphosphate disodium salt, hexahydrate | 1.25 | mg. |
| Nicotinamide adenine dinucleotide phosphate, disodium salt | 1.17 | mg. |
| Adenosine monophosphate, disodium salt | 8.47 | mg. |
| Hexokinase | 5 | U. |
| Glucose-6-phosphate dehydrogenase | 3 | U. |
| Glucose | 8.32 | mg. |
| Magnesium acetate | 4.52 | mg. |

-continued

| The bottle with the buffer solution contains: | | |
|---|---|---|
| Triethanolamine acetate (in water) | 105 | mM |

The lyophilized antibodies are dissolved in 2 ml. of distilled water. The thus-formed antibody solution is adjusted so that up to 1000 U./l. of CK-MM is totally inhibited. In case of sera having extremely high total CK activities, the serum must, therefore, be preliminarily diluted to about 1000 U/l. The antibody solution can be preserved at +4° C. for at least 7 days.

(b) Conductance of the Activity Analysis of CK-MB ($b_1$) Execution

Introduce into a reaction vessel by means of a pipette:
0.1 ml. serum
+0.1 ml. antibody solution.
Mix well, incubate for 5 minutes at 25° C. Then, introduce 0.1 ml. of this reaction mixture, as well as 2.0 ml. of buffer solution, into a bottle with the mixture of coenzyme, enzyme, and substrate. Mix this solution, incubate same at 25° C. for 5 minutes, then pour into a cuvette, measure the extinction at 25° C., and thereafter determine the change in extinction per minute. Wavelength: 334, 340, or 366 nm.; layer thickness: 1 cm.

($b_2$) Calculation

The thus-determined CK activity of the sample must be multiplied by
(a) the dilution factor: 2
and
(b) the CK-MB hybrid factor: 2
(in the test, only the B subunits of CK-MB are measured).

From the change in extinction per minute ($\Delta E$/minute) the average value is determined and inserted in the appropriate calculation formula:*

*Compare "Methoden der enzymatischen Analyse", edited by H. U. Bergmeyer, 3rd edition (1974), page 331 et seq.

Measurement at 334 nm.: volume activity CK-MB = $\Delta E$/minute $\times 4 \times 35000$ U./l.
Measurement at 340 nm.: volume activity CK-MB = $\Delta E$/minute $\times 4 \times 3376$ U./l.
Measurement at 366 nm.: volume activity CK-MB = $\Delta E$/minute $\times 4 \times 6364$ U./l.

Application Example II

Test II for the quantitative determination of the creatinekinase-MB activity in body fluids.

(a) Composition of the Test Kit

The test kit is sufficient for 30 activity analyses. The kit contains 1 bottle of buffer solution for 30 analyses and 30 bottles of a lyophilized mixture consisting of coenzyme, enzyme, substrate, and anti-CK-MM according to Example 1.

The amount of triethanolamine acetate contained in the bottle with the buffer solution corresponds to the amount indicated in Application Example I($a$). The individual bottles containing the mixture consisting of coenzyme, enzyme, substrate, and anti-CK-MM according to Example 1 likewise correspond to the composition indicated in Application Example I($a$) with respect to the three first-mentioned components and additionally contain anti-CK-MM totally inhibiting up to 1000 U./l. CK-MM.

(b) Determination of the Activity of CK-MB ($b_1$) Execution

Add by means of a pipette 2.0 ml. of buffer solution and 0.1 ml. of serum to the content of a bottle of coenzyme/enzyme/substrate/anti-CK-MM mixture. Mix the solution, incubate same for 5 minutes at 25° C., then pour into a curvette and measure the extinctions at 25° C. over a period of 5 minutes. Wavelength: 334, 340, or 366 nm.; layer thickness: 1 cm.

($b_2$) Calculation

The average value is formed from the changes in extinction per minute ($\Delta E$/minute) and inserted in the corresponding calculation formula:
Measurement at 334 nm.: volume activity CK-MB = $\Delta E$/minute $\times 7000$ U./l.
Measurement at 340 nm.: volume activity CK-MB = $\Delta E$/minute $\times 6752$ U./l.
Measurement at 366 nm.: volume activity Ck-MB = $\Delta E$/minute $\times 12728$ U./l.

Application Example III

Simultaneous analysis of the total CK activity and of the CK-MB activity.

(a) Composition of the Test Kit

The composition of the test kit corresponds to that of Application Example I(a).

(b) Determination of the Total CK Activity and of the CK-MB Activity ($b_1$) Execution Introduce by means of a pipette 2.0 ml. of buffer solution and 0.1 ml. of serum or diluted serum into the bottle with the coenzyme/enzyme/substrate mixture. Mix the solution, incubate same for 5 minutes at 25° C., then pour the mixture into a cuvette and measure the change in extinction ($\Delta E1$) for 2 min. at 25° C. Then add 0.1 ml. of antibody solution, mix immediately, and again determine the change in extinction ($\Delta E2$) at 25° C. after 3 minutes. Wavelength: 334, 340, or 366 nm.; layer thickness: 1 cm.

($b_2$) Calculation

The total CK activity is calculated as follows:
Measurement at 334 nm.: volume activity CK-total = $\Delta E1$/minute $\times 3500$ U./l.
Measurement at 340 nm.: volume activity CK-total = $\Delta E1$/minute $\times 3376$ U./l.
Measurement at 366 nm.: volume activity CK-total = $\Delta E1$/minute $\times 6364$ U./l.

The CK-MB activity can be obtained according to the following calculation formulae:
Measurement at 334 nm.: volume activity CK-MB = $\Delta E2$/minute $\times 7350$ U./l.
Measurement at 340 nm.: volume activity CK-MB = $\Delta E2$/minute $\times 7090$ U./l.
Measurement at 366 nm.: volume activity CK-MB = $\Delta E2$/minute $\times 13364$ U./l.

Application Example IV

Inhibition of the activity of CK-MM, CK-MB, and CK-BB by anti-human-CK-MM.

Pure CK-MM, CK-MB, or CK-BB is added to a human serum inactivated with regard to its inherent CK activity, and the CK activities of the individual samples are determined. Thereafter, 0.1 ml. of the sample is combined with 0.1 ml. of anti-CK-MM solution, prepared, for example, according to Example 1. The substances are mixed and incubated for 5 minutes at 25° C. Then, the residual CK activity is determined in a conventional manner. The results are set forth in the following table: Residual Activities of CK Isoenzymes after Incubation with Inhibiting Anti-Human-CK-MM (Average Values ±1 s from Respectively Five-Fold Analyses) (s=Standard Deviation)

TABLE

| Isoenzyme | Activity Added (U./l.) | Residual Activity after Incubation with Anti-CK-MM (U./l.) |
|---|---|---|
| CK-MM | 98 ± 1.9 | 0.3 ± 2.1 |
| | 1043 ± 22 | 0.5 ± 2.5 |
| CK-MB | 103 ± 2.0 | 53 ± 1.7 |
| | 410 ± 7.8 | 206 ± 6.2 |
| CK-BB | 197 ± 3.8 | 199 ± 4.1 |

Within the measuring accuracy range, the activities of CK-MM are inhibited to an extent of 100%, those of CK-BB to an extent of 0%, and those of CK-MB (corresponding to the proportion of 50% M subunits) to an extent of 50%. The results are constant over a wide activity range of the added isoenzyme activities.

Application Example V

Determination of CK-MB activities in patients with and without cardiac infarction with a test kit according to Example I(a).

CK activities of various collective groups of patients:

| | Number of Cases | Average Values | |
|---|---|---|---|
| | | Total CK (U./l.) | CK-MB (U./l.) |
| Patients with increased CK activities without cardiac infarctions | 48 | 480 | <1.7 |
| Patients with cardiac infarctions | 5 | 510 | 44 |

The table shows that it is possible to obtain rapidly and unequivocally an indication of the presence of a cardiac infarction with the aid of the antibodies according to the present invention.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Antibodies having a molecular weight of 130,000–210,000 and a sedimentation constant between 6S and 8S; and being capable of effecting in creatinekinase-MM (CK-MM) and creatinekinase-MB (CK-MB) complete inhibition of enzymatic activity of the M subunit without inhibiting the enzymatic activity of the B subunit and without precipitation; wherein complete inhibition of the enzymatic activity of said M subunit of creatinekinase leaves less than 5 U./l. of said enzymatic activity intact, and non-inhibition of said enzymatic activity of said B subunit is less than 10 U./l., and wherein said antibodies are substantially free of creatinekinase-BB (CK-BB) isoenzyme activity; wherein said antibodies are prepared by the steps of activating a CK-MM antigen from skeletal muscle of humans, monkeys, pigs or cattle by an activator for —SH groups selected from the group consisting of N-acetylcysteine, mercaptoethanol, dithioerythritol, glutathione, cysteine, dithiothreitol, S-(2-aminoethyl)-isothiouronium bromide hydrobromide and thioglycolic acid or a divalent metal ion activator selected from the group consisting of magnesium, manganese, calcium and cobalt, or a mixture of activators; inoculating a goat with the thus-activated CK-MM antigen; withdrawing blood from the goat; and isolating said antibodies from the withdrawn blood.

2. The antibodies of claim 1, which are able to effect complete inhibition of said enzymatic activity of said M subunit in CK-MM and CK-MB without inhibiting said enzymatic activity of said B subunit, even in the presence of CK substrate.

3. The antibodies of claim 1, wherein the CK-MM antigen is activated by dialysis against the activator in the presence of a dialysis buffer for 1–200 hours at 1°–30° C.

4. The antibodies of claim 1, wherein 10–500 mM of activator is used per mg. of creatinekinase-MM being activated.

5. The antibodies of claim 1, wherein the activator is magnesium ions.

6. The antibodies of claim 1, wherein the activator is N-acetylcysteine, mercaptoethanol or dithioerythritol.

7. The antibodies of claim 1, wherein the activator is magnesium ions and N-acetylcysteine, mercaptoethanol or dithioerythritol.

8. The antibodies of claim 7, wherein the CK-MM is activated by dialysis against the activator in the presence of a dialysis buffer for 1–200 hours at 1°–30° C.;
10–500 mM of activator is used per mg. of creatinekinase-MM being activated; and
the activator is magnesium ions and N-acetylcysteine mercaptoethanol or dithioerythritol.

9. The antibodies of claim 8, wherein the CK-MM antigen is from human skeletal muscle.

10. The antibodies of claim 1, which have a molecular weight of 160,000–180,000 and a sedimentation constant of about 7S and wherein complete inhibition of the enzyme activity of said M subunit of creatinekinase leaves less than 3 U./l. of said enzymatic activity intact and non-inhibition of said enzymatic activity of said B subunit is less than 5 U./l.

11. The antibodies of claim 10, which are antihuman skeletal muscle CK-MM.

12. In the method for producing creatinekinase-MM (CK-MM) antibodies with a molecular weight of 130,000–210,000 and a sedimentation constant between 6S and 8S consisting of the steps of inoculating an animal with a CK-MM antigen; withdrawing blood from the animal; and isolating said antibodies from the withdrawn blood, the improvement which comprises activating the CK-MM antigen, just prior to inoculation, with an activator for —SH groups selected from the group consisting of N-acetylcysteine, mercaptoethanol, dithioerythritol, glutathione, cysteine, dithiothreitol, S-(2-aminoethyl)-isothiouronium bromide hydrobromide and thioglycolic acid or a divalent metal ion activator selected from the group consisting of magnesium, manganese, calcium and cobalt, or a mixture of activators; wherein the CK-MM antigen is from skeletal muscle of humans, monkeys, pigs, or cattle, and the inoculated animal is a goat.

13. The method of claim 12, wherein the CK-MM antigen is activated by dialysis against the activator in the presence of a dialysis buffer for 1-200 hours at 1°-30° C.

14. The method of claim 12, wherein 10-500 mM of activator is used per mg. of creatinekinase-MM being activated.

15. The method of claim 12, wherein the activator is magnesium ions.

16. The method of claim 12, wherein the activator is N-acetylcysteine, mercaptoethanol or dithioerythritol.

17. The method of claim 12, wherein the activator is magnesium ions and N-acetylcysteine, mercaptoethanol or dithioerythritol.

18. The method of claim 12, wherein the CK-MM antigen is activated by dialysis against the activator in the presence of a dialysis buffer for 1-200 hours at 1°-30° C.;

10-500 mM of activator is used per mg. of creatinekinase-MM being activated; and the activator is magnesium ions and N-acetylcysteine, mercaptoethanol or dithioerythritol.

* * * * *